US012680127B2

(12) United States Patent
Huang et al.

(10) Patent No.: US 12,680,127 B2
(45) Date of Patent: Jul. 14, 2026

(54) METHOD FOR POLYMERASE CHAIN REACTION

(71) Applicant: NATIONAL CHENG KUNG UNIVERSITY, Tainan City (TW)

(72) Inventors: Chih-Chia Huang, Tainan City (TW); Dar-Bin Shieh, Tainan City (TW); Li-Xing Yang, New Taipei City (TW); Chien-Wei Lee, Tainan City (TW)

(73) Assignee: NATIONAL CHENG KUNG UNIVERSITY, Tainan City (TW)

( * ) Notice: Subject to any disclaimer, the term of this patent is extended or adjusted under 35 U.S.C. 154(b) by 425 days.

(21) Appl. No.: 18/263,577

(22) PCT Filed: Jan. 28, 2022

(86) PCT No.: PCT/CN2022/074585

§ 371 (c)(1),
(2) Date: Jul. 31, 2023

(87) PCT Pub. No.: WO2022/161460

PCT Pub. Date: Aug. 4, 2022

(65) Prior Publication Data

US 2025/0283159 A1 Sep. 11, 2025

Related U.S. Application Data

(60) Provisional application No. 63/143,946, filed on Jan. 31, 2021.

(51) Int. Cl.
*C12Q 1/68* (2018.01)
*C12Q 1/6848* (2018.01)
*C12Q 1/686* (2018.01)

(52) U.S. Cl.
CPC ........... *C12Q 1/6848* (2013.01); *C12Q 1/686* (2013.01)

(58) Field of Classification Search
CPC .............................. C12Q 1/6848; C12Q 1/686
See application file for complete search history.

(56) References Cited

U.S. PATENT DOCUMENTS

| | | | |
|---|---|---|---|
| 8,034,633 B2 | 10/2011 | Geddes | |
| 9,062,254 B2 | 6/2015 | Zhou et al. | |
| 10,213,785 B2 | 2/2019 | Shieh et al. | |
| 10,604,798 B2 | 3/2020 | Roche et al. | |
| 2009/0208919 A1* | 8/2009 | Utermohlen | C12N 5/0634 |
| | | | 252/182.33 |
| 2010/0028983 A1 | 2/2010 | Geddes | |
| 2013/0214206 A1 | 8/2013 | Zhou et al. | |
| 2016/0060672 A1 | 3/2016 | Shieh et al. | |
| 2019/0048397 A1 | 2/2019 | Roche et al. | |

FOREIGN PATENT DOCUMENTS

| | | |
|---|---|---|
| CN | 105948128 A | 9/2016 |
| CN | 106795555 A | 5/2017 |
| CN | 108883417 A | 11/2018 |
| CN | 111373011 A | 7/2020 |
| TW | 201619391 A | 6/2016 |
| TW | 202014385 A | 4/2020 |
| WO | 2019216134 A | 11/2019 |

OTHER PUBLICATIONS

Zhang et al. Enhancement of the polymerase chain reaction by tungsten disulfide. Royal Society of Chemistry Advances, 2019, 9, pp. 9373-9378 (Year: 2019).*
International Search Report issued in International Application No. PCT/CN2022/074585, with English translation (May 7, 2022).
Tolessa Fita Chala, "National Taiwan University of Science and Technology, Oral test date: Jan. 15, 2019", retrieved from URL: https://hdl.handle.net/11296/uttvpj on Jul. 31, 2023, English abstract only.
Sandhya Songara, et al., "Tuning of crystal phase structure in hydrated WO3 nanoparticles under wet chemical conditions and studies on their photochromic properties," Journal of Physics and Chemistry of Solids, v. 73, pp. 851-857 (2012).

* cited by examiner

*Primary Examiner* — Jezia Riley
(74) *Attorney, Agent, or Firm* — MCBEE MOORE & VANIK IP, LLC

(57) ABSTRACT

Disclosed in the present invention is a method for polymerase chain reaction. In the method, tungsten oxide nanoparticles having a specific transmittance in the infrared spectrum are irradiated with an electromagnetic wave with a specific wavelength, such that a low concentration of tungsten oxide nanoparticles can quickly heat a reaction solution, thereby shortening the heating time, and improving the efficiency of the polymerase chain reaction.

9 Claims, 7 Drawing Sheets

Specification includes a Sequence Listing.

100

110

Mix a plurality of tungsten oxide nanoparticles, a nucleic acid fragment and a reaction reagent to form a reaction solution

120

Irradiate these tungsten oxide nanoparticles with an electromagnetic wave to subject the reaction solution to the polymerase chain reaction and amplify a portion of the sequence of the nucleic acid fragment

METHOD FOR POLYMERASE CHAIN REACTION

RELATED APPLICATIONS

This application is the U.S. national phase under § 371 of International application No. PCT/CN2022/074585, filed Jan. 28, 2022 which claims the benefits of priority of U.S. Provisional Application Ser. No. 63/143,946 filed Jan. 31, 2021, the content of which are incorporated herein by reference in their entireties.

BACKGROUND

A sequence listing is being submitted herein as an ASCII text file with the name "SP-5290-US_SEQ_LIST.txt", created on Mar. 5, 2024, with a file size of 4,096 bytes.

FIELD OF INVENTION

The present invention relates to a method for polymerase chain reaction, and in particular, to a method for polymerase chain reaction using tungsten oxide nanoparticles.

DESCRIPTION OF RELATED ART

The conventional polymerase chain reaction (PCR) involves separating complementary double strands of a nucleic acid fragment (commonly referred to as a template DNA) by heating (i.e., a denaturation step), then targeting a pair of primers (i.e., a forward primer and a reverse primer) to nucleic acid sequences complementary to the sequences of the individual primers (i.e., an annealing step) in the nucleic acid fragment, and then replicating a new nucleic acid product (commonly referred to as an amplicon) through primer-guided extension by a polymerase according to the nucleic acid sequences of the nucleic acid fragment (i.e., an extension step). Each cycle typically consists of the aforementioned three steps (the denaturation step, the annealing step and the extension step) in sequence. After one cycle, the next cycle is performed by the succeeding aforementioned denaturation step and other steps until the nucleic acid product reaches a desired amount.

For example, in conventional PCR, the temperature of the denature step is first kept at 95° C. for 15 sec to 30 sec, and then the temperature of the annealing step is reduced to an appropriate annealing temperature for 30 sec to 60 sec. Then, the temperature of the extension step is performed at 70° C. to 75° C. for usually 30 sec to 60 sec, and the time of the extension step depends on the length of the nucleic acid fragment to be amplified. The denaturation can be completed instantly in the aforementioned denaturation step, and the polymerization efficiency of the polymerase in the extension step can also be increased by precisely controlling the heating of a reaction solution. However, conventional PCR instruments achieve thermal equilibrium by using metal heating components or water, and their heating rates cannot meet the requirement of the temperature change for the denaturation step and the extension step, resulting in lengthy heating time and energy consumption.

In view of this, there is an urgent need to develop a new method for polymerase chain reaction to improve the above-mentioned shortcomings of the conventional polymerase chain reaction.

SUMMARY

In view of the above problems, an aspect of the present invention is to provide a method for polymerase chain reaction. In the method, an electromagnetic wave with a specific wavelength is used to irradiate tungsten oxide nanoparticles having a specific transmittance in the infrared spectrum, such that a low concentration of tungsten oxide nanoparticles can quickly heat a reaction solution, thereby shortening the heating time.

According to an aspect of the present invention, a method for polymerase chain reaction is provided. In the method, a plurality of tungsten oxide nanoparticles, a nucleic acid fragment and a reaction reagent are mixed to form a reaction solution, in which after mixing, a concentration of these tungsten oxide nanoparticles is 50 ppm to 1000 ppm, and a first transmittance of these tungsten oxide nanoparticles in a first wavelength range of greater than 780 nm and not greater than 2000 nm is less than 98%. Then, the reaction solution is subjected to the polymerase chain reaction to amplify a portion of a sequence of the nucleic acid fragment, in which in the polymerase chain reaction, the reaction solution is irradiated with an electromagnetic wave to perform a denaturation step and an extension step, and a wavelength of the electromagnetic wave is 400 nm to 2000 nm.

According to an embodiment of the present invention, a second transmittance of these tungsten oxide nanoparticles in a wavelength range of 380 nm to 780 nm is greater than 40%.

According to another embodiment of the present invention, a third transmittance of these tungsten oxide nanoparticles in a wavelength range from 400 nm to 600 nm is not less than 50%.

According to another embodiment of the present invention, a fourth transmittance of these tungsten oxide nanoparticles in a fourth wavelength range of greater than 780 nm and not greater than 1100 nm is not greater than 95%.

According to yet another embodiment of the present invention, each of these tungsten oxide nanoparticles includes a plurality of tungsten oxide nanorods, each of these tungsten oxide nanorods has an average length and an average diameter, and a ratio of the average length to the average diameter being 5 to 25.

According to yet another embodiment of the present invention, these tungsten oxide nanoparticles have a general formula (I) $W_aO_b$, in the general formula (I), W represents tungsten, O represents oxygen, and a ratio of b to a (b/a) is 1 to 3.

According to yet another embodiment of the present invention, these tungsten oxide nanoparticles have a general formula (II) $W_aO_bM_c$, in which general formula (II), W represents tungsten, O represents oxygen, M represents nickel, palladium, platinum or a combination thereof, and a ratio of b to the sum of a and c [b/(a+c)] is 1 to 3.

According to yet another embodiment of the present invention, an average heating rate of the denaturation step and the extension step is 2° C./sec to 23° C./sec.

According to yet another embodiment of the present invention, a heating time of the denaturation step and the extension step is not greater than 15 sec.

According to yet another embodiment of the present invention, a power of the electromagnetic wave is 0.1 W to 2 W.

By applying the method for polymerase chain reaction of the present invention, in which the tungsten oxide nanoparticles having the specific transmittance in the infrared spectrum are irradiated with the electromagnetic wave with the specific wavelength, the low concentration of tungsten oxide nanoparticles can quickly heat the reaction solution, thereby shortening the heating time, so as to improve the efficiency of the polymerase chain reaction.

BRIEF DESCRIPTION OF THE DRAWINGS

In order to have a more complete understanding of the embodiments of the present invention and their advantages, now please refer to the following description together with the accompanying drawings. It must be emphasized that various features are not drawn to scale and are for illustration purpose only. The contents of the relevant drawings are described below.

DETAILED DESCRIPTION

The manufacturing and using of embodiments of the present invention are discussed in detail below. However, it should be appreciated that the embodiments provide many applicable inventive concepts that can be embodied in a wide variety of specific contexts. The specific embodiments discussed are illustrative only, and are not intended to limit the scope of the invention.

In a method for polymerase chain reaction of the present invention, tungsten oxide nanoparticles having a specific transmittance in the infrared spectrum are irradiated with an electromagnetic wave with a specific wavelength, so that a low concentration of tungsten oxide nanoparticles can quickly heat a reaction solution, thereby shortening the heating time, so as to improve the efficiency of the polymerase chain reaction. In addition, these tungsten oxide nanoparticles have a high transmittance in the visible light spectrum to reduce the absorption of excitation light and radiated light of a fluorescent agent in the reaction reagent, thereby reducing the background interference of the polymerase chain reaction.

Figure 1:
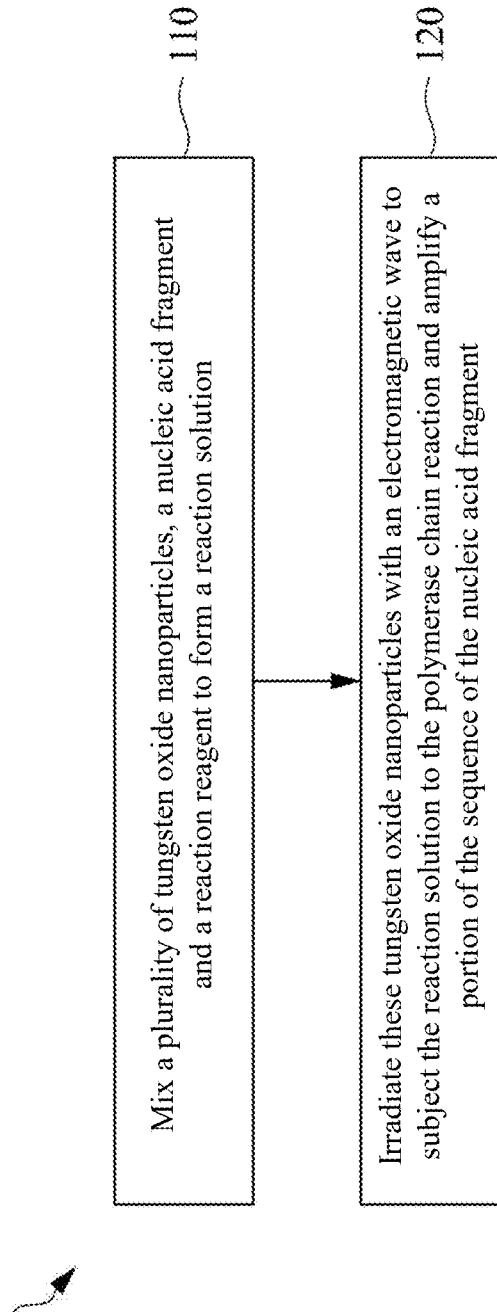
FIG. 1 illustrates a flowchart of a method for polymerase chain reaction according to an embodiment of the present invention.

Referring to FIG. 1, in the method for polymerase chain reaction 100, a plurality of tungsten oxide nanoparticles, a nucleic acid fragment and a reaction reagent are first mixed to form a reaction solution, as shown in an operation 110. Since tungsten oxide nanoparticles have the ability of light-to-heat conversion, they can convert the absorbed electromagnetic wave into heat energy to heat the reaction solution.

A transmittance of the tungsten oxide nanoparticles in a wavelength range of greater than 780 nm and not greater than 2000 nm is less than 98%. Equivalently, the absorption of the tungsten oxide nanoparticles in the infrared spectrum is not less than 2%. If the absorption of the tungsten oxide nanoparticles in the infrared spectrum is less than 2%, the tungsten oxide nanoparticles cannot effectively absorb the electromagnetic wave to convert it into heat energy, so the reaction solution cannot be heated effectively. Preferably, a transmittance of the tungsten oxide nanoparticles in a wavelength range of greater than 780 nm and not greater than 1100 nm is not greater than 95%.

Further, the reaction solution containing a fluorescent agent is used in the method for polymerase chain reaction 100. After being irradiated by the excitation light, the fluorescent agent emits fluorescence that is used to detect the amount of a nucleic acid product. Therefore, the fluorescent agent can be used to quantify the original amount of the nucleic acid fragment. The less the interference of the added tungsten oxide nanoparticles with the absorption of the excitation light and the radiated fluorescence of the fluorescent agent is, the more the accuracy and/or sensitivity of the quantifying subsequent to the method for polymerase chain reaction can be improved.

Furthermore, the wavelengths of the excitation light and the radiated light of the fluorescent agent are usually in the visible light spectrum, so the accuracy and/or sensitivity of the quantification subsequent to the method for polymerase chain reaction can be improved by controlling a transmittance of the tungsten oxide nanoparticles in the visible light spectrum. In some embodiments, a transmittance of the tungsten oxide nanoparticles in a wavelength range from 380 nm to 780 nm (which is equivalent to the visible light spectrum) is greater than 40%. Preferably, a transmittance of the tungsten oxide nanoparticles in a wavelength range from 400 nm to 600 nm is not less than 50%. In some specific embodiments, a transmittance of the tungsten oxide nanoparticles in a portion of wavelengths of the wavelength range of the visible light spectrum is greater than 40%, for example, 450 nm, 500 nm, 550 nm and combinations thereof (such as 450 nm to 550 nm or 500 nm to 550 nm). However, in some other embodiments, the tungsten oxide nanoparticles can have an absorption in the visible light spectrum except in the wavelength ranges of the excitation light and the fluorescence, or the absorption in the wavelength ranges of the excitation light and the fluorescence is very low, for example, the absorption is less than 28%, preferably less than 20%, and more preferably less than 10%, so that the excitation light and the fluorescence will not be interfered. Furthermore, the aforementioned tungsten oxide nanoparticles can also convert the absorbed visible light into heat energy to heat the reaction solution.

Accordingly, in the aforementioned embodiments, the method for polymerase chain reaction 100 of the present invention can exclude a step of gel electrophoresis that removes the tungsten oxide nanoparticles by the gel electrophoresis, thereby simplifying the subsequent step that quantifies the amount of the nucleic acid fragment. However, in some other embodiments, the step of gel electrophoresis can be optionally performed in the method for polymerase chain reaction to remove the tungsten oxide nanoparticles before the subsequent step that quantifies the amount of the nucleic acid fragment, so as to further improve the accuracy and/or sensitivity of the quantification.

The tungsten oxide nanoparticles can have various shapes, for example, spherical, rod-like, linear or columnar. In some embodiments, the tungsten oxide nanoparticles can be, but be not limited to, tungsten oxide nanorods. The tungsten oxide nanorods can have an average length and an average diameter, in which the average length can be 250 nm to 550 nm, and the average diameter can be 20 nm to 50 nm. The aforementioned average diameter can also be called an average width when viewing from a cross-section passing through the long axis of the nanorods.

In some specific embodiments, a ratio of the average length to the average diameter can be 5 to 25. The aforementioned ratio of the average length to the average diameter is also referred to as an aspect ratio. Preferably, the aspect ratio can be 6 to 23. When the aspect ratio is in the aforementioned range, the absorption peak of the tungsten oxide nanoparticles moves towards a shorter wavelength (such as, moves to the infrared spectrum), thereby reducing or eliminating the absorption in the visible spectrum, thus reducing the interference with the fluorescence emission of the fluorescent agent.

In some embodiments, the tungsten oxide nanoparticles have a general formula (I) $W_aO_b$, in which the general formula (I), W represents tungsten, O represents oxygen, and a ratio of b to a (b/a) is 1 to 3. When the tungsten oxide nanoparticles have the general formula (I), the tungsten oxide nanoparticles have an absorption in the infrared spectrum to enhance the ability of light-to-heat conversion of the tungsten oxide nanoparticles. The ratio of b to a is preferably greater than 2 and less than 3, in which oxygen atoms of the tungsten oxide nanoparticles are insufficient. Therefore, free electrons exist, and the absorption of the infrared light by the tungsten oxide nanoparticles is enhanced, thereby improving the ability of light-to-heat conversion of the tungsten oxide nanoparticles.

In addition to oxygen and tungsten, the constituent elements of the tungsten oxide nanoparticles can optionally include Group VIII transition metal elements. In other words, the material of the tungsten oxide nanoparticles includes undoped tungsten oxide and doped tungsten oxide, and these doped transition metal elements can enhance the absorption of the infrared light by the tungsten oxide nanoparticles, thereby improving the ability of light-to-heat conversion of these nanoparticles.

For example, in some embodiments, the tungsten oxide nanoparticles have a general formula (II) $W_aO_bM_c$, in which general formula (II), W represents tungsten, O represents oxygen, M represents nickel, palladium, platinum or a combination thereof, and a ratio of b to the sum of a and c [b/(a+c)] is 1 to 3. When the ratio of b to the sum of a and c is in the aforementioned range, the absorption of the infrared light by the tungsten oxide nanoparticles is further enhanced, thereby improving the ability of light-to-heat conversion of these nanoparticles.

In addition, the aforementioned nucleic acid fragment is used as a template DNA. The nucleic acid fragment in the present invention is not particularly limited, and can be known to a person of ordinary skill in the art of the present invention. For example, the nucleic acid fragment can include nucleic acids from infectious microorganisms, such as bacteria, viruses, fungi, and parasites.

Furthermore, the aforementioned reaction reagent can include a polymerase, a pair of primers, a nucleotide base, a fluorescent agent and a buffer solution, all of which are known to a person of ordinary skill in the art of the present invention. As it is understood by a person of ordinary skill in the art, the design of the pair of primers should be based on the sequence of the aforementioned nucleic acid fragment, so that the primer can be annealed to a single strand of the nucleic acid fragment, which in turn achieves the purpose of polymerase chain reaction.

In the reaction solution formed by the tungsten oxide nanoparticles, the nucleic acid fragment and the reaction reagent, the concentration of the tungsten oxide nanoparticles is 50 ppm to 1000 ppm. If the concentration of the tungsten oxide nanoparticles is less than 50 ppm, tungsten oxide nanoparticles will be not enough to effectively heat the reaction solution, and the heating time cannot be shorten. Conversely, if the concentration of the tungsten oxide nanoparticles is greater than 1000 ppm, excessive tungsten oxide nanoparticles will greatly reduce the transmittance in the visible light region, thereby interfering with the fluorescence radiated by the fluorescent agent, and thus the amount of the nucleic acid fragment cannot be quantified. Further, the concentration of the tungsten oxide nanoparticles can preferably be 50 ppm to 500 ppm, and more preferably can be 300 ppm to 350 ppm.

After the operation 110, in the method for polymerase chain reaction 100, the reaction solution is subjected to the polymerase chain reaction to amplify a portion of the sequence of the nucleic acid fragment, as shown in an operation 120. In the aforementioned polymerase chain reaction, the reaction solution is irradiated with an electromagnetic wave to perform the denaturation step and the extension step. In the denaturation step and the extension step, the electromagnetic wave irradiates the tungsten oxide nanoparticles in the reaction solution, so that the tungsten oxide nanoparticles absorb the electromagnetic wave and then generate heat energy which can heat the reaction solution.

The wavelength of the electromagnetic wave is 400 nm to 2000 nm, i.e., the frequency of the electromagnetic wave is 150 THz to 750 THz. In other words, the electromagnetic wave includes visible light, near-infrared rays, and far-infrared rays. Since the electromagnetic wave is absorbed by the tungsten oxide nanoparticles, the absorption properties of the tungsten oxide nanoparticles determine the wavelength of the electromagnetic wave. As previously described, the absorption properties of the tungsten oxide nanoparticles can be affected by shape and dopants. For example, in some embodiments, the wavelength of the electromagnetic wave can be 780 nm to 2000 nm, so that the tungsten oxide nanorods absorbing the near-infrared rays generate heat energy to heat the reaction solution. Similarly, the tungsten oxide nanoparticles absorbing the visible light can also heat the reaction solution under the irradiation of the visible light.

In addition, the power of the electromagnetic wave will affect the heating rate of the reaction solution by the tungsten oxide nanoparticles, in which the greater the power is, the greater the heating rate will be, and vice versa. In some embodiments, the power of the electromagnetic wave can be 0.1 W to 2 W. When the power of the electromagnetic wave is in the aforementioned range, the electromagnetic wave having this power is able to make the tungsten oxide nanoparticles generate enough heat energy quickly, so that the average heating rate meets the temperature change requirements of the denaturation step and the extension step, thereby shortening the heating time, and by precisely controlling the heating of the reaction solution, the polymerization efficiency of the polymerase is improved.

In some embodiments, the average heating rate of the denaturation step and the extension step is 2° C./sec to 23° C./sec. The average heating rate in the aforementioned range can meet the requirement to heat rapidly during the denaturation step, so as to shorten the heating time. Thus, the heating in the extension step is precisely controlled to improve, thereby improving the polymerization efficiency of the polymerase and thus the efficiency of the polymerase chain reaction. In some specific embodiments, the heating times of the denaturation step and the extension step are not greater than 15 sec. Preferably, the heating times of the denaturation step and the extension step can be 5 sec to 15 sec and 1 sec to 4 sec, respectively. When the heating time is in the aforementioned range, the heating time can be further shortened, thereby improving the efficiency of the polymerase chain reaction. Preferably, the heating times of the denaturation step and the extension step are not greater than 10 sec.

Examples are used to illustrate the application of the present invention below, but they are not intended to limit the present invention. Anyone skilled in the art should make various variations and modifications without departing from the spirit and scope of the present invention.

Manufacture Nanoparticles

Example 1

Tungsten oxide nanorods of Example 1 were prepared by a hydrothermal method, in which 1 mg to 300 mg of halide of tungsten, 1 mL to 20 ml of 0.1 M to 1.5 M hydrochloric acid and 1 mL to 20 mL ink (an aqueous solution including polyethylene glycol (PEG), ethylene glycol (EG), polyvinylpyrrolidone (PVP) and glycerin) were mixed to obtain a mixture, and then the mixture was reduced with 0.01 mL to 1 mL of $N_2H_4$ to obtain the tungsten oxide nanorods of Example 1. Then, an evaluation was performed by an evaluation method described later.

Examples 2 to 3 and Comparative Example 1

Doped tungsten oxide nanorods of Examples 2 to 3 and iron oxide nanoparticles of Comparative Example 1 were all manufactured by a method similar to that of Example 1. The difference was that in Examples 2 to 3, the halide of tungsten was reduced, and in Example 2, 0.1 mg to 80 mg of a halide of platinum was added, while in Example 3, 0.1 mg to 80 mg of a halide of palladium was added. In addition, a halide of iron was used instead of the halide of tungsten in Comparative Example 1. The evaluation results of the aforementioned Examples 1 to 3 and Comparative Example 1 were shown in Table 1 below.

Evaluation Methods

1. Test of Transmittance of Tungsten Oxide Nanoparticles

In the test of transmittance, the spectrum transmitting the tungsten oxide nanoparticles was measured using a spectrometer. The spectrum included the visible light spectrum and the infrared spectrum, and the test conditions were those conventionally used by those skilled in the art.

2. Test of Size of Tungsten Oxide Nanoparticles

In the test of size, the size, such as, the particle size, of the tungsten oxide nanoparticles was measured by an electron microscope, in which the test conditions were those conventionally used by those skilled in the art. When the tungsten oxide nanoparticles were tungsten oxide nanorods, the size included an average length and an average diameter, and the ratio of the average length to the average diameter (which was also called an aspect ratio, and was rounded) was obtained.

3. Test of Element Contents of Tungsten Oxide Nanoparticles

The test of element contents was carried out with a chemical element analyzer, and the general composition formula of the tungsten oxide nanoparticles was calculated from the measured element contents, in which the test conditions were those conventionally used by those skilled in the art.

4. Comparison Test of Heating Rates of Different Nanoparticles

Figure 2:
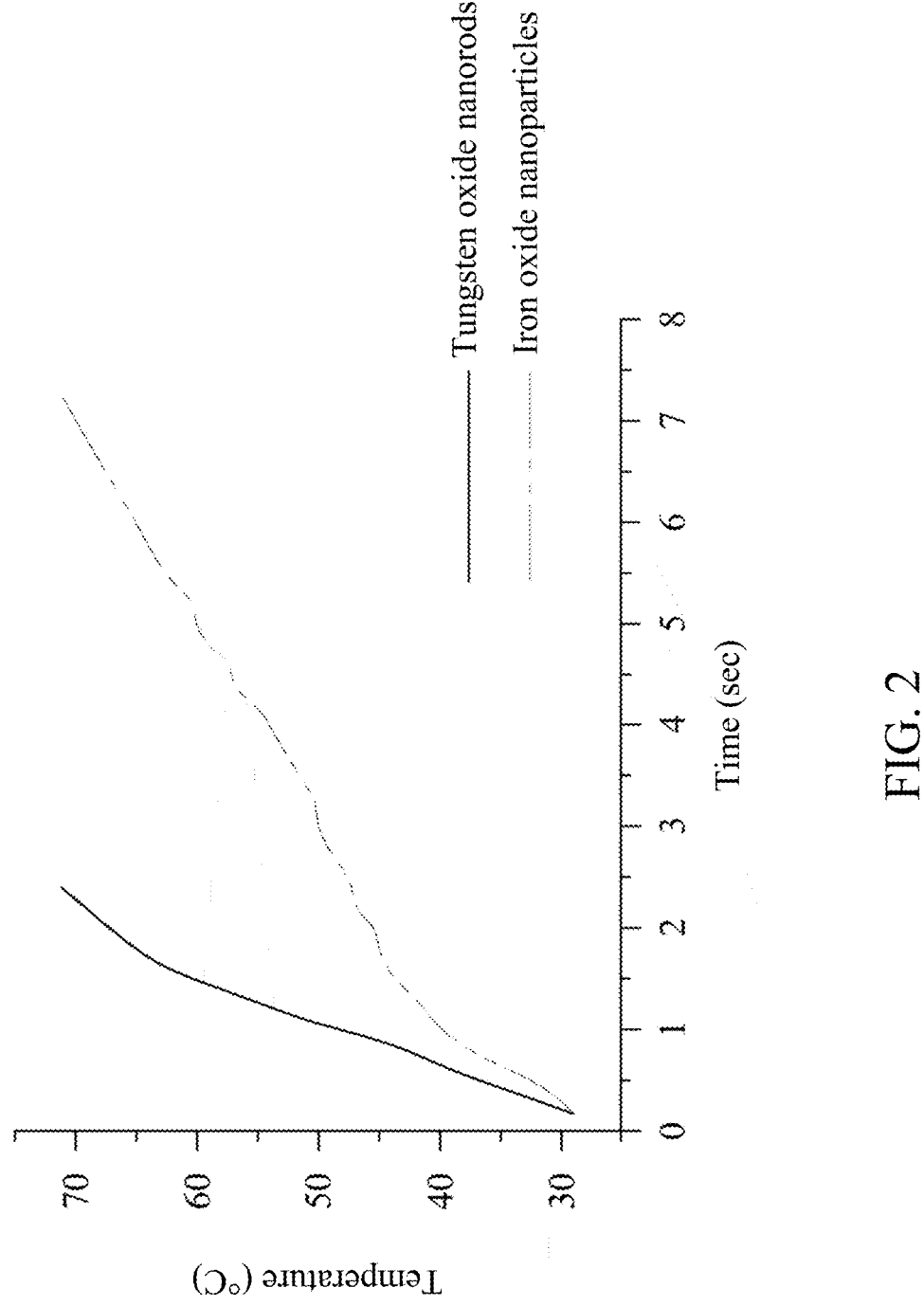
FIG. 2 illustrates temperature change curves when a reaction reagent is heated using nanoparticles of Example 1 and Comparative Example 1 of the present invention respectively.
Figure 3:
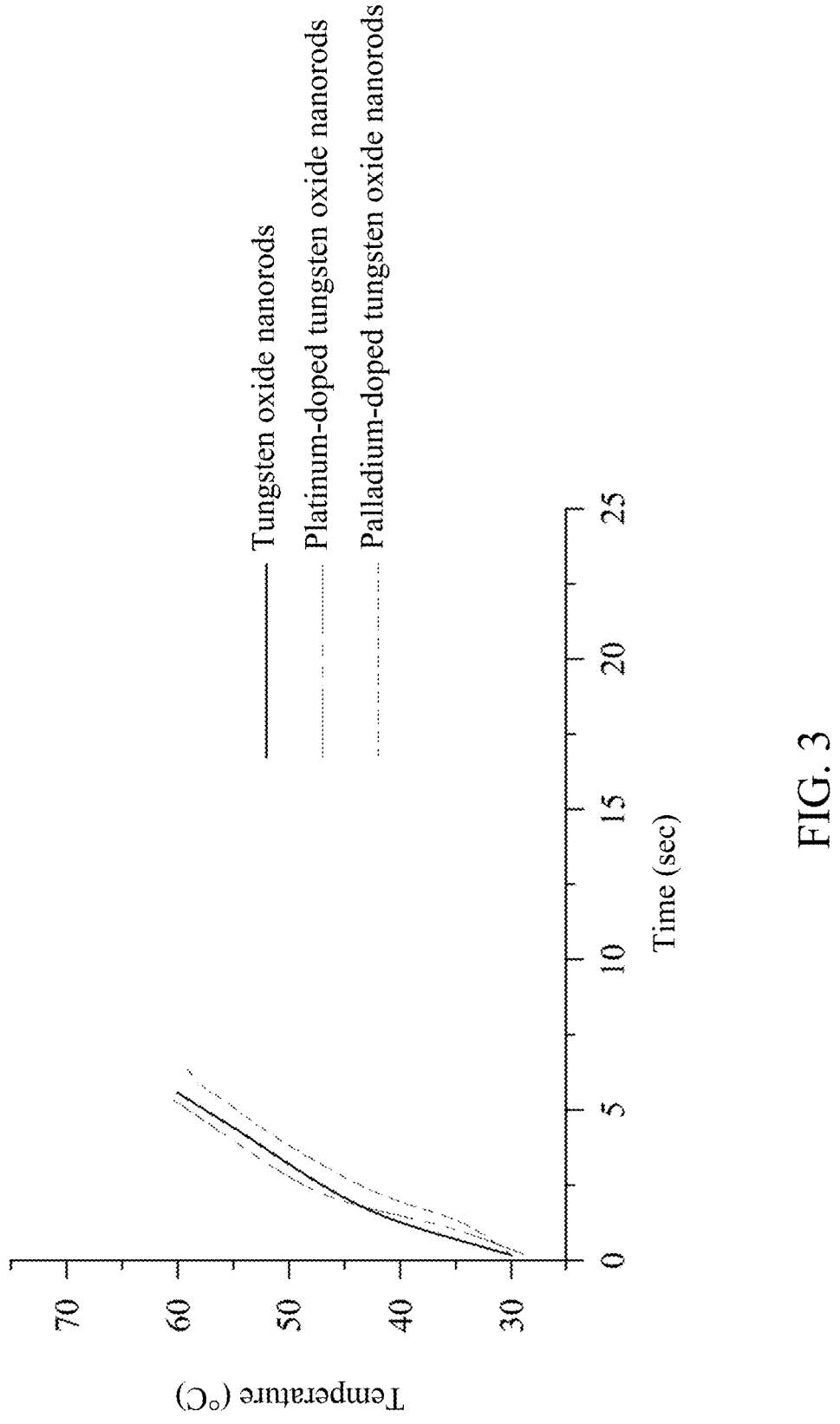
FIG. 3 illustrates temperature change curves when the reaction reagent is heated using nanoparticles of Example 1 to Example 3 of the present invention respectively.

In the comparison test of heating rates, the nanoparticles prepared in Examples 1 to 3 and Comparative Example 1 were added into reaction reagents with a volume of 20 μL respectively. Then, these reaction reagents containing nanoparticles were irradiated with an electromagnetic wave having a wavelength of 808 nm and a power of 1 W for heating. Temperature change curves of these reaction reagents were recorded, as shown in FIG. 2 and FIG. 3. The temperature difference of heating from 28° C. to 60° C. (i.e., 32° C.) was divided by the required time intervals to obtain average heating rates. The results were shown in Table 1.

5. Tests of Interference 5.1 Interference Test of Amplification Reaction

The interference test of amplification reaction was carried out in polymerase chain reactions similar and identical to that of the subsequent Application Example 1. In the polymerase chain reaction identical to that of the subsequent Application Example 1, the tungsten oxide nanorods were used and the electromagnetic wave was irradiated, and in the polymerase chain reaction similar to that of the subsequent Application Example 1, differences were that no tungsten oxide nanorods were used or no electromagnetic wave was irradiated. Thus, it could find out whether the tungsten oxide nanorods could heat the reaction solution by being irradiated with the electromagnetic wave, and whether the heating of the heated reaction solution could make the polymerase perform the polymerase chain reaction. In addition, it could also find out whether these tungsten oxide nanorods had no effect on the nucleic acid amplification reaction of the polymerase.

In particular, tungsten oxide nanorods with concentrations of 660 ppm and 330 ppm were used, respectively, and the reaction solutions were irradiated with an electromagnetic wave having a programmed wavelength of $8.08 \times 10^2$ nm to subject the reaction solutions to the polymerase chain reaction. As an electromagnetic wave with a power of 1 W was turned on, the reaction solutions were heated from 25° C. to 95° C. at an average heating rate of 5° C./sec to 10° C./sec (with a heating time of 7 sec to 15 sec); after the power of the electromagnetic wave was reduced, the denaturation step was performed for 1 sec to 30 sec while the temperature was maintained; after the electromagnetic wave was turned off and an fan was turned on to reduce the temperature to 56° C., the annealing step was performed for 1 sec to 30 sec while the temperature was maintained; and then after the electromagnetic wave with the power of 1 W was turned on to heat the reaction solutions at an average heating rate of 5° C./sec to 10° C./sec (with a heating time of 1.6 to 3.2 sec) to 72° C., the extension step was performed for 1 sec to 30 sec while the temperature was maintained. A cycle consisted of the aforementioned three steps in sequence, and the polymerase chain reactions was terminated after repeating the cycle for 40 times. That is, when the amplification of a portion of the sequence of the amplified nucleic acid fragment was completed, a nucleic acid product could be obtained. Then, gel electrophoresis was performed on the obtained nucleic acid product. From the result of electrophoresis, it could find out whether the heating of the reaction solutions could be control by irradiating the tungsten oxide nanorods with the electromagnetic wave, whether the polymerase could perform the polymerase chain reaction, and whether these tungsten oxide nanorods would not affect the nucleic acid amplification reaction of the polymerase. The results were shown in FIG. 4.

5.2 Comparison Test of Background Interferences of Different Nanoparticles

In the comparison test of background interferences, the nanoparticles prepared in Example 1 and Comparative Example 1 were added into reaction reagents with a volume of 20 µL, respectively. The reaction reagents containing nanoparticles were irradiated with an excitation light having a wavelength of 488 nm, and the intensity of the fluorescence emitted by the reaction reagents containing nanoparticles at a wavelength of 520 nm were measured. The results were shown in Table 1 and FIG. 5, and the intensity of fluorescence of the reaction reagents with no nanoparticles added was measured and used as a 100% baseline to obtain the intensity of fluorescence of the reaction reagent with the nanoparticles added.

of the pair of primers had a sequence as shown by SEQ ID NO: 1, and the reverse primer had a sequence as shown by SEQ ID NO: 2.

Figure 6:
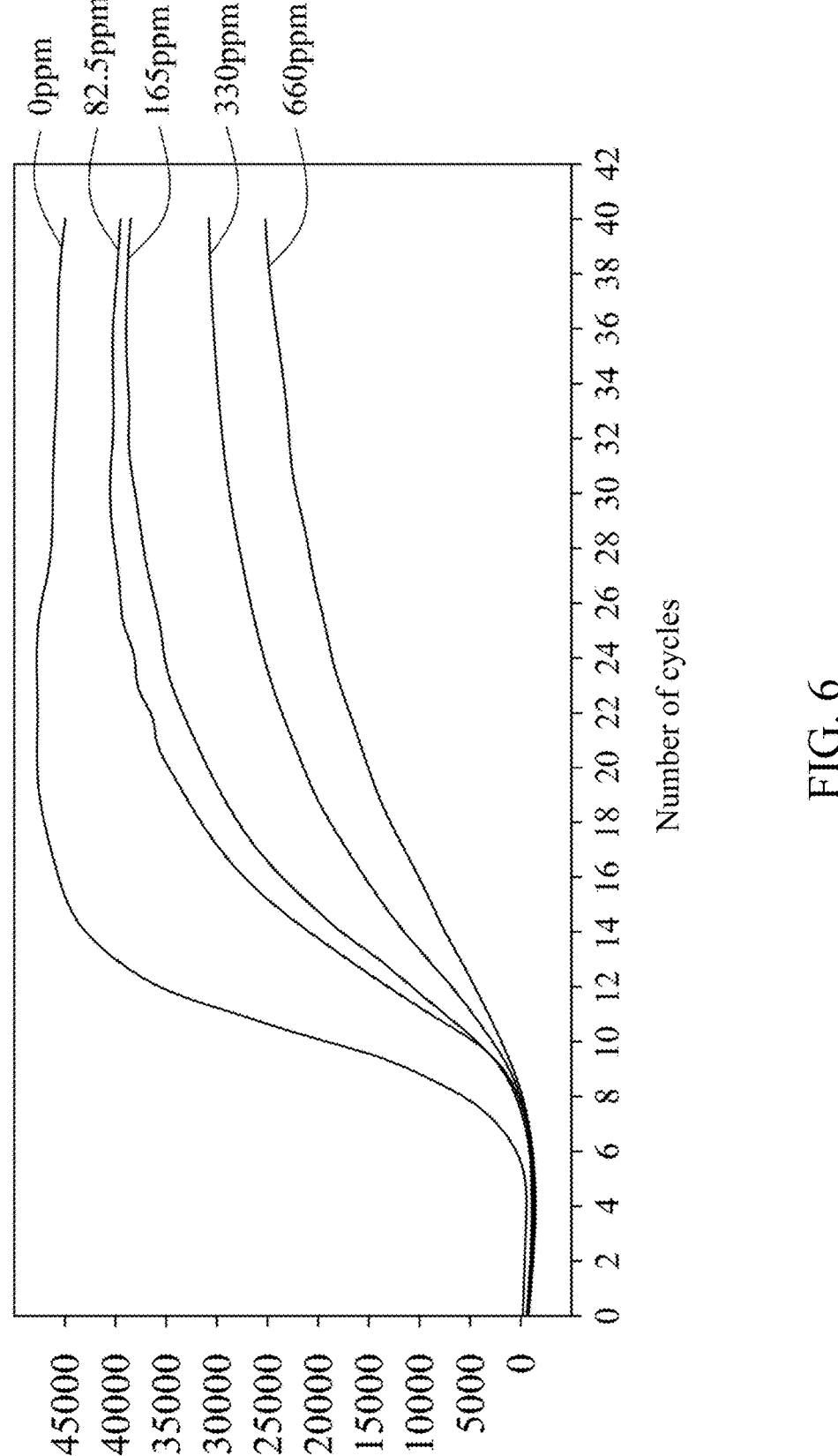
FIG. 6 illustrates increase curves of a method for polymerase chain reaction according to Application Example 1 of the present invention.

Then, the polymerase chain reaction was performed by a real-time detection polymerase chain reaction machine. Using the same reaction temperature and time conditions as those of the aforementioned interference test of amplification reaction, the polymerase chain reaction was terminated after a desired number of cycles (as shown in FIG. 6) were repeated, that is, amplification of a portion of the sequence of the amplified nucleic acid fragment was completed, thereby obtaining a nucleic acid product. At the end of each cycle, the fluorescence signal of the amplified nucleic acid product was detected, and the increased signal difference $\Delta Rn$ was calculated. The obtained fluorescence signal increase curves were shown in FIG. 6. In addition, it should be noted that the fan used in the temperature reduction step

TABLE 1

| | | | Example | | | Comparative |
|---|---|---|---|---|---|---|
| | | | 1 | 2 | 3 | Example 1 |
| Materials | Nanoparticles | | Tungsten Oxide Nanorods | Platinum-Doped Tungsten Oxide Nanorods | Palladium-Doped Tungsten Oxide Nanorods | Iron Oxide Nanoparticles |
| Evaluation Results: | Transmittance (%) | 450 nm | 75 | 72 | 94 | 69 |
| | | 500 nm | 85 | 82 | 95 | 79 |
| | | 550 nm | 92 | 87 | 95 | 85 |
| | | 800 nm | 92 | 96 | 97 | 99 |
| | | 900 nm | 91 | 96 | 97 | 99 |
| | | 1000 nm | 90 | 93 | 97 | 99 |
| | | 1100 nm | 87 | 93 | 97 | 99 |
| | Size | Average Length (nm) | 297-507 | 297-507 | 297-507 | Spherical (60-150) |
| | | Average Diameter (nm) | 25-47 | 25-47 | 25-47 | |
| | | Aspect Ratio | 6-20 | 6-20 | 6-20 | |
| | Element Content | General Formula | $W_aO_b$ $b/a = 1$-$3$ | $W_aO_bPt_c$ $b/(a + c) = 1$-$3$ | $W_aO_bPd_c$ $b/(a + c) = 1$-$3$ | |
| | Average Heating Rate (° C./sec) | 1000 ppm | 21.3 | N/A | N/A | 6.1 |
| | | 330 ppm | 6.4 | 6.4 | 5.3 | N/A |
| | Background Interference (%) | 250 ppm | 5 | N/A | N/A | 34 |
| | | 500 ppm | 2.5 | N/A | N/A | 37 |
| | | 1000 ppm | 1.3 | N/A | N/A | 36 |

Note:
"N/A" meant that the test was not conducted.
Method for Polymerase chain reaction

Application Example 1

In Application Example 1, the aforementioned tungsten oxide nanorods prepared in Example 1 were used to perform the polymerase chain reaction, in which the tungsten oxide nanorods, a nucleic acid fragment and a reaction reagent were mixed to form a reaction solution with a volume of 20 µL. In particular, the reaction reagent included a polymerase, a pair of primers, a nucleotide base, a fluorescent agent and a buffer solution, in which the polymerase, the nucleotide base, the fluorescent agent and the buffer solution used a reagent manufactured by Roche (the brand name was KAPA SYBR FAST qPCR kit), and the reaction reagent was added according to the instructions of this product. Furthermore, taking a nucleic acid extract of genetically transformed *Escherichia coli* as an example, the concentration of the nucleic acid fragment was 0.1 µg/mL, the added volume of the nucleic acid fragment was 1 µL, and the forward primer of the polymerase chain reaction of Application Example 1 was the same as that of conventional PCR instruments for temperature reduction, and the conditions of the temperature reduction step could be the same as those of the conventional PCR instruments, so details were not repeated here.

Comparative Application Example 1

Comparative Application Example 1 was carried out by a method similar to that of Application Example 1. The difference was that in Comparative Application Example 1, iron oxide nanoparticles were used instead of the tungsten oxide nanorods, and the increase curves were shown in FIG. 7.

According to the results of the transmittance and average heating rate in Table 1, and FIG. 2 to FIG. 3, the transmittances of the tungsten oxide nanomaterials of Examples 1 to 3 at 800 nm to 1100 nm were lower than that of the iron oxide nanoparticles of Comparative Example 1, so the nanomaterials of Examples 1 to 3 could absorb the electromagnetic wave having a wavelength of 800 nm to 1100 nm (e.g., the infrared light), and convert it into heat energy to heat the reaction solution, thereby increasing the average heating rate. Accordingly, the nanomaterials of Examples 1 to 3 could heat the reaction solution more quickly to be advantageous to a more effective control on the temperatures of the reaction solution in the denaturation step and the extension step, such as a shortening heating time, thereby improving the efficiency of the polymerase chain reaction.

Secondly, referring to the results of the element content in Table 1, both the platinum-doped tungsten oxide nanorods in Example 2 and the palladium-doped tungsten oxide nanorods in Example 3 could increase oxygen vacancies by the doped transition metals, thereby increasing free electrons that could increase the absorption of the nanomaterials in the infrared spectrum (that is, reduce the transmittance in the infrared spectrum), resulting in an improving light-to-heat conversion rate of the nanomaterials.

Further, according to the results of the size and average heating rate in Table 1, and FIG. 2 to FIG. 3, compared to the spherical iron oxide nanoparticles in Comparative Example 1, the nanomaterials in Examples 1 to 3 were all rod-shaped with an aspect ratio. With the aspect ratio of 5 to 25, the nanorods could further increase the light-to-heat conversion rate of the nanomaterials, so the temperature of the reaction solution in the denaturation step and the extension step could be controlled more effectively.

Figure 4:
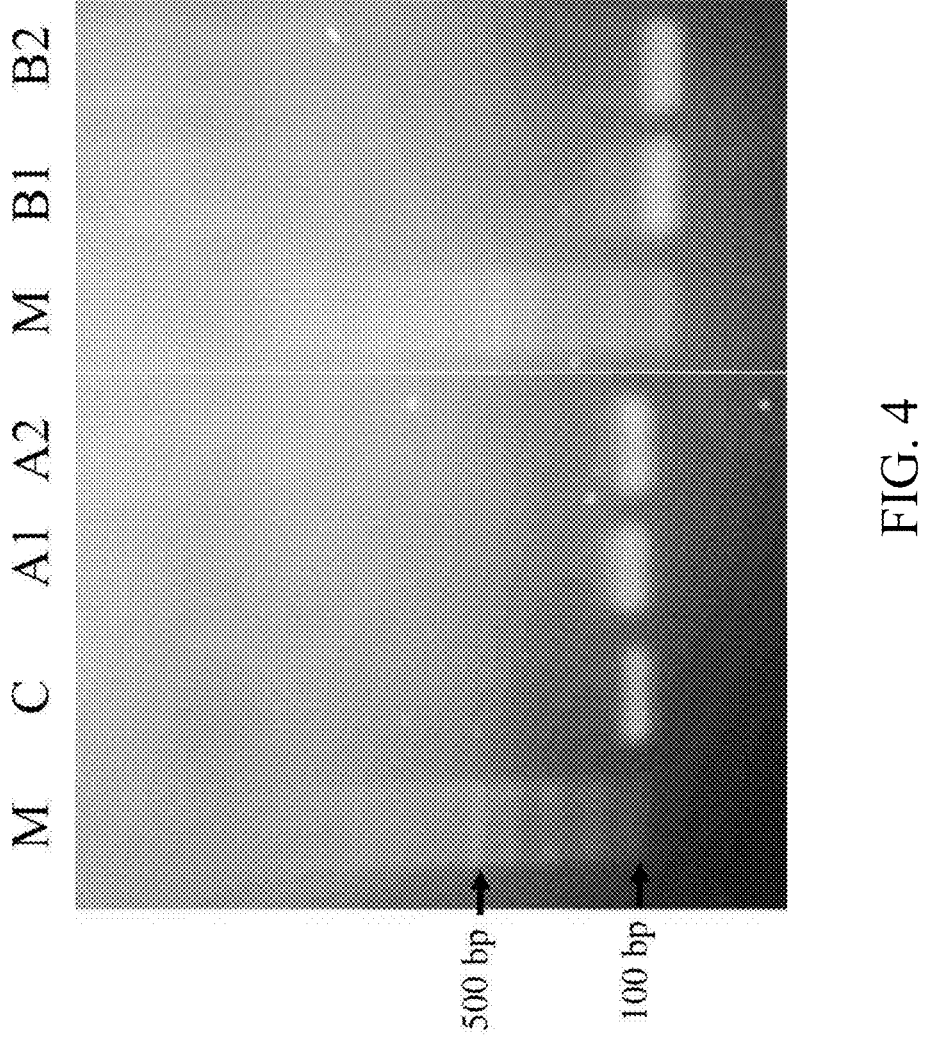
FIG. 4 illustrates an image of an electrophoresis film of an interference comparison test for a traditional polymerase chain reaction (a polymerase chain reaction without using an electromagnetic wave) and a polymerase chain reaction with the electromagnetic wave using the nanoparticles of Example 1 of the present invention respectively.

In addition, according to FIG. 4, "M" represented a standard product, "C" represented a nucleic acid product obtained by a method for polymerase chain reaction with no nanoparticles were used, "A1" represented a nucleic acid product obtained by a method for polymerase chain reaction using 660 ppm of tungsten oxide nanorods irradiated by an 808 nm electromagnetic wave, "A2" represented a nucleic acid product obtained by a method for polymerase chain reaction using 330 ppm of tungsten oxide nanorods irradiated by an 808 nm electromagnetic wave, "B1" represented a nucleic acid product obtained by a method for polymerase chain reaction using 660 ppm of tungsten oxide nanorods not irradiated by electromagnetic wave, and "B2" represented a nucleic acid product obtained by a method for polymerase chain reaction using 330 ppm of tungsten oxide nanorods not irradiated by electromagnetic wave.

In particular, the tungsten oxide nanorods of Example 1 with concentrations of 660 ppm and 330 ppm were used for the method for polymerase chain reaction, and the nucleic acid products obtained by the method were the same as the nucleic acid product obtained by performing the method without the nanomaterials, that is, both has a base pair length of 100 bp. Secondly, through the analysis of the image of the electrophoresis film, the brightness of the nucleic acid product obtained by using 330 ppm of tungsten oxide nanorods was consistent with the brightness of the nucleic acid product obtained by using 660 ppm of tungsten oxide nanorods. Accordingly, the added tungsten oxide nanorods would not affect the nucleic acid amplification reaction of the polymerase.

Figure 5:
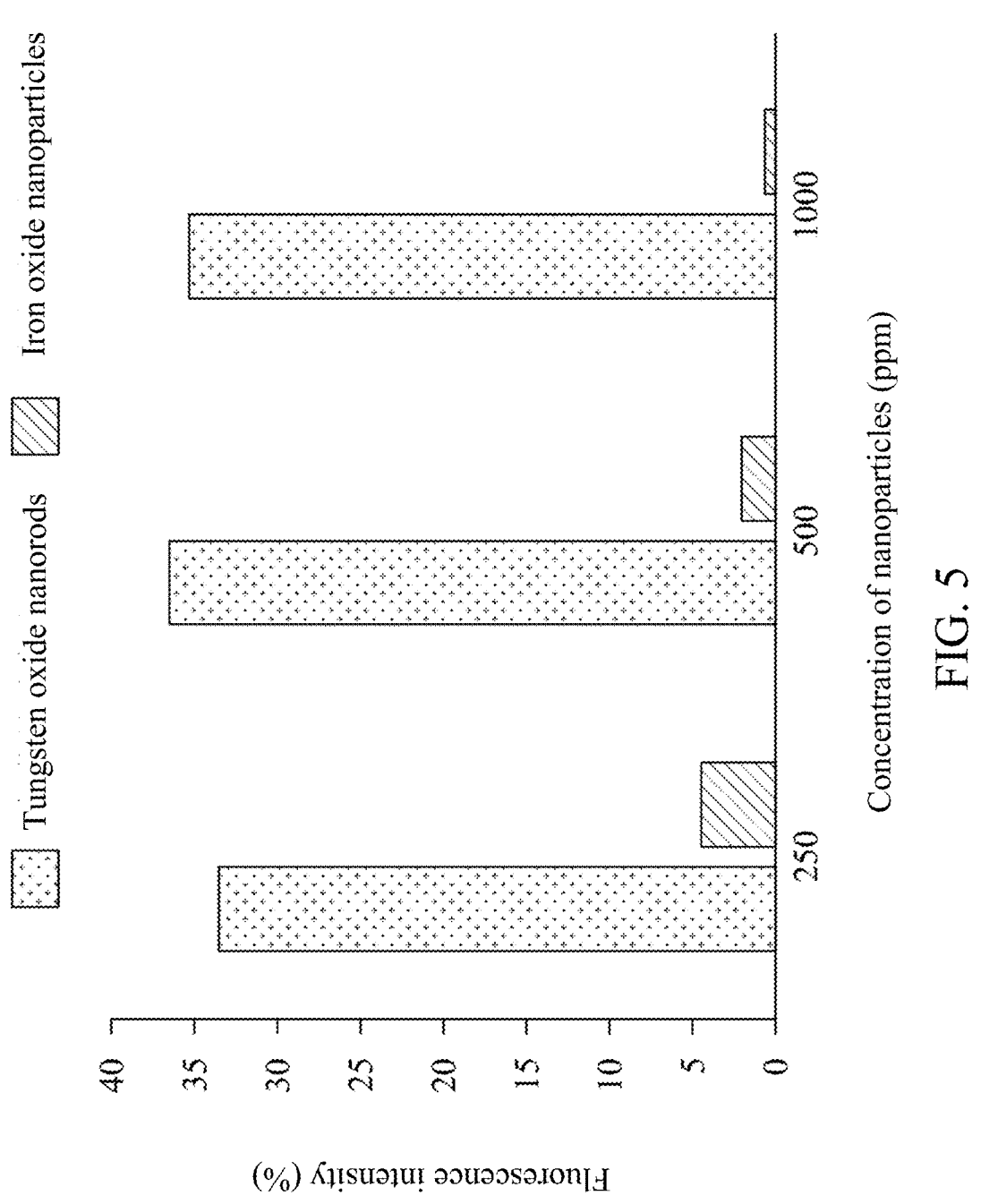
FIG. 5 illustrates a graph of the results of a comparison test of background interference using the nanoparticles of Example 1 and Comparative Example 1 of the present invention respectively.

Further, according to the results of the transmittance and background interference in Table 1, and FIG. 5, the transmittances of the tungsten oxide nanomaterials of Examples 1 to 3 at 450 nm to 550 nm were higher than that of the iron oxide nanoparticles of Comparative Example 1, indicating that the nanomaterials of Examples 1 to 3 had a lower absorption of an electromagnetic wave with a wavelength of 450 nm to 550 nm (e.g., the visible light), and thus could reduce the absorption of the excitation light and radiated light of the fluorescent agent in the reaction reagent, thereby reducing the background interference. Further, according to the results of background interference, after calculation (by rounding off), the background interference produced by the iron oxide nanoparticles of Comparative Example 1 was 7 to 28 times higher than the background interference produced by the tungsten oxide nanorods of Example 1.

Figure 7:
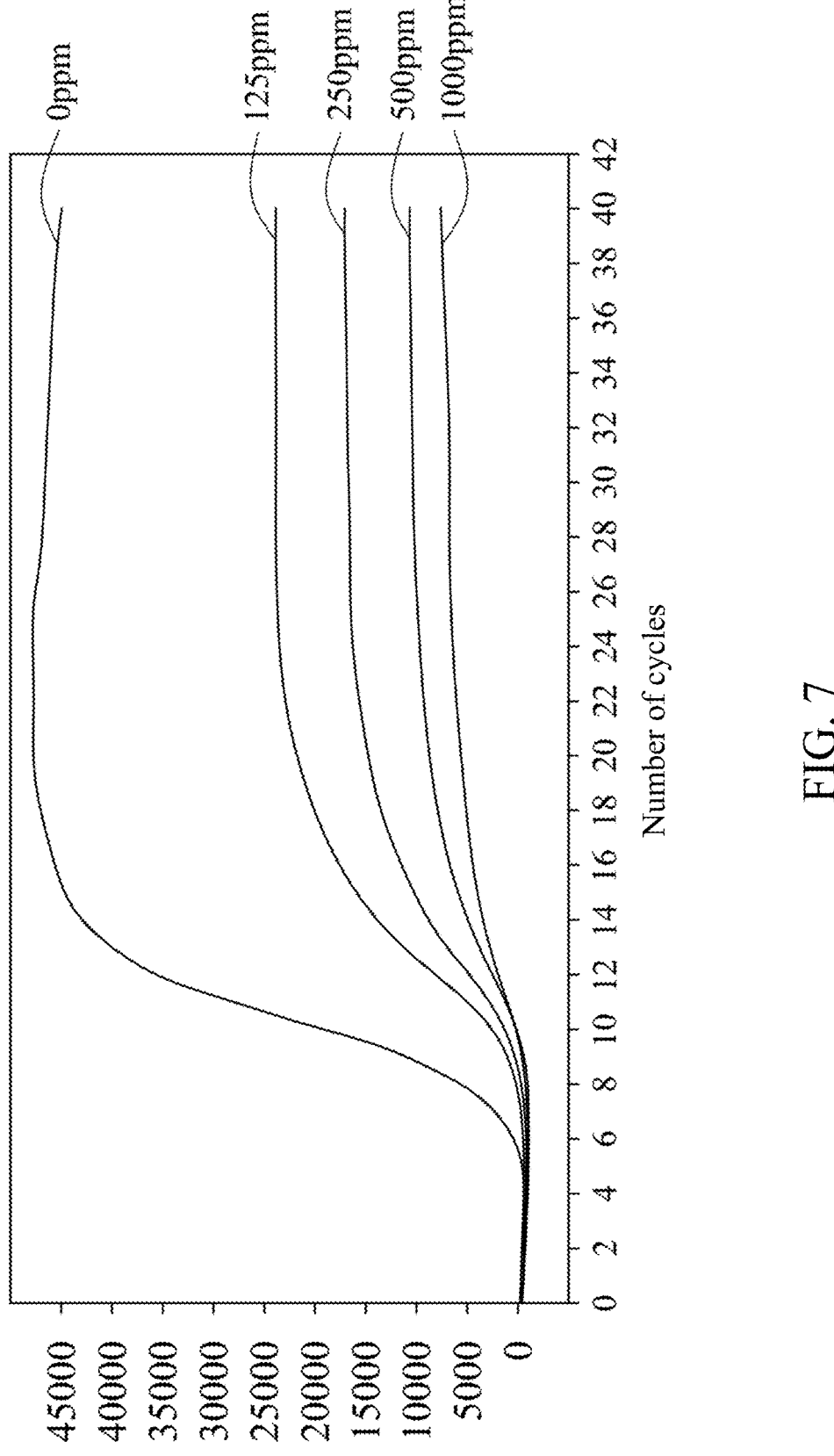
FIG. 7 illustrates increase curves of a method for polymerase chain reaction according to Comparative Application Example 1 of the present invention.

Then, according to FIG. 6 and FIG. 7, "ΔRn" represented the difference in the fluorescence intensities of the reaction solution containing nanomaterials before and after the nucleic acid amplification reaction. All the PCR reactions could be carried out using 82.5 ppm to 660 ppm of the tungsten oxide nanorods of Example 1. However, to achieve a similar ΔRn fluorescence intensity difference to that of 660 ppm of tungsten oxide nanoparticles (about 25000), the iron oxide nanoparticles of Comparative Example 1 should be as low as 125 ppm. Accordingly, since the tungsten oxide nanorods had a better light transmittance, the interference of the tungsten oxide nanorods with the detection of the fluorescence of the nucleic acid product could be reduced. Further, when the concentration of the tungsten oxide nanorods was 660 ppm, the maximum ΔRn was 25000, while when the concentration of the iron oxide nanoparticles was 125 ppm, their maximum ΔRn was 24000. If the ΔRn of the two were considered to be equivalent, the ratio of the concentrations of the two is 5.28 (660/125=5.68), from which it was also found that the method using the tungsten oxide nanorods of Example 1 had a lower interference.

In conclusion, in a method for polymerase chain reaction of the present invention, tungsten oxide nanoparticles having a specific transmittance in the infrared spectrum are irradiated with an electromagnetic wave of a specific wavelength, such that a low concentration of tungsten oxide nanoparticles can quickly heat a reaction solution, thereby shortening the heating time, and improving the efficiency of the polymerase chain reaction.

Although the present invention has been disclosed as above with embodiments, these embodiments are not intended to define the present invention. Anyone skilled in the art should make various variations and modifications without departing from the spirit and scope of the present invention. Therefore, the scope of protection of the invention shall be subject to the scope defined in the attached claims.

---

What is claimed is:

1. A method for polymerase chain reaction, comprising:
mixing a plurality of tungsten oxide nanoparticles, a nucleic acid fragment and a reaction reagent to form a reaction solution, wherein after mixing, a concentration of the plurality of tungsten oxide nanoparticles is 50 ppm to smaller than 1000 ppm, and a first transmittance of the plurality of tungsten oxide nanoparticles in a first wavelength range of greater than 780 nm and not greater than 2000 nm is less than 98%, and a second transmittance of the plurality of tungsten oxide nanoparticles in a second wavelength range of 380 nm to 780 nm is greater than 40%; and
subjecting the reaction solution to the polymerase chain reaction to amplify a portion of a sequence of the nucleic acid fragment, wherein in the polymerase chain reaction, the reaction solution is irradiated with an electromagnetic wave to perform a denaturation step and an extension step, and a wavelength of the electromagnetic wave is 400 nm to 2000 nm.

2. The method for polymerase chain reaction according to claim 1, wherein a third transmittance of the plurality of tungsten oxide nanoparticles in a third wavelength range of 400 nm to 600 nm is not less than 50%.

3. The method for polymerase chain reaction according to claim 1, wherein a fourth transmittance of the plurality of tungsten oxide nanoparticles in a fourth wavelength range of greater than 780 nm and not greater than 1100 nm is not greater than 95%.

4. The method for polymerase chain reaction according to claim 1, wherein the plurality of tungsten oxide nanoparticles comprise a plurality of tungsten oxide nanorods, each of the plurality of tungsten oxide nanorods has an average length and an average diameter, and a ratio of the average length to the average diameter is 5 to 25.

5. The method for polymerase chain reaction according to claim 1, wherein the plurality of tungsten oxide nanoparticles have a general formula (I) $W_aO_b$, in the general formula (I), W represents tungsten, O represents oxygen, and a ratio of b to a (b/a) is 1 to 3.

6. The method for polymerase chain reaction according to claim 1, wherein the plurality of tungsten oxide nanoparticles have a general formula (II) $W_aO_bM_c$, in the general formula (II), W represents tungsten, O represents oxygen, M represents nickel, palladium, platinum or a combination thereof, and a ratio of b to a sum of a and c [b/(a+c)] is 1 to 3.

7. The method for polymerase chain reaction according to claim 1, wherein an average heating rate of the denaturation step and the extension step is 2° C./sec to 23° C./sec.

8. The method for polymerase chain reaction according to claim 1, wherein a heating time of the denaturation step and the extension step is not greater than 15 sec.

9. The method for polymerase chain reaction according to claim 1, wherein a power of the electromagnetic wave is 0.1 W to 2 W.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: synthetic construct
<220> FEATURE:
<223> OTHER INFORMATION: forward primer -continued

```
<400> SEQUENCE: 1
gcgaaagtcc tggttgagct gag                                        23

<210> SEQ ID NO 2
<211> LENGTH: 21
<212> TYPE: DNA
<213> ORGANISM: synthetic construct
<220> FEATURE:
<223> OTHER INFORMATION: reverse primer

<400> SEQUENCE: 2
aacccaaggc ccatgcatac a                                          21
```